(12) United States Patent
Haas

(10) Patent No.: US 8,728,464 B2
(45) Date of Patent: May 20, 2014

(54) METHOD FOR STIMULATING OSTEOGENESIS

(75) Inventor: Jamie Haas, Pinehurst, ID (US)

(73) Assignee: University of Idaho, Moscow, ID (US)

( * ) Notice: Subject to any disclaimer, the term of this patent is extended or adjusted under 35 U.S.C. 154(b) by 0 days.

(21) Appl. No.: 13/135,933

(22) Filed: Jul. 19, 2011

(65) Prior Publication Data

US 2012/0141429 A1 Jun. 7, 2012

Related U.S. Application Data

(60) Provisional application No. 61/419,152, filed on Dec. 2, 2010.

(51) Int. Cl.
*C12C 1/00* (2006.01)
*C12N 5/00* (2006.01)

(52) U.S. Cl.
USPC .......................................... 424/93.7; 435/395

(58) Field of Classification Search
USPC .......................................... 424/93.7; 435/395
See application file for complete search history.

(56) References Cited

U.S. PATENT DOCUMENTS

| | | | |
|---|---|---|---|
| 7,759,165 B1 | 7/2010 | Bajaj | |
| 7,771,512 B2 | 8/2010 | Norton | |
| 7,972,616 B2 * | 7/2011 | Dubrow et al. | ............... 424/423 |
| 2006/0204738 A1 | 9/2006 | Dubrow | |
| 2010/0215915 A1 | 8/2010 | Norton | |
| 2010/0255447 A1 | 10/2010 | Biris | |
| 2011/0201984 A1 * | 8/2011 | Dubrow et al. | ................. 602/54 |

FOREIGN PATENT DOCUMENTS

| | | |
|---|---|---|
| WO | WO 2007/002369 | 1/2007 |
| WO | WO 2010/132879 | 11/2010 |
| WO | WO 2011/050345 | 4/2011 |

OTHER PUBLICATIONS

Oh et al. (Significantly accelerated osteoblast cell growth on aligned TiO2 nanotubes. 2006. J. Biomed. Mater. Res. 78A 97-103).*
The University of Idaho Department of Physics (Nanomaterials for Biological Research, pp. 1-3).*
McIlroy, DN, et al, "Nanosprings," Applied Physics Letters, 79 (10):1540-1542 (2001).
Sai, Vvr, et al, "Silica Nanosprings Coated with Noble Metal Nanoparticles: Highly Active SERS Substrates," J. Phys. Chem. C, 115:453-459 (2011).
Ruckh, T, et al, "Nanostructured Tantala as a Template for Enhanced Osseointegration," Nanotechnology, 20:045012 (7 pp) (2009).
Oh, S, et al, "Significantly accelerated osteoblast cell growth on aligned TiO2 nanotubes," J. Biomed. Mater. Res., 78A:97-103 (2006).
Streicher, MS, et al, "Nanosurfaces and Nanostructures for Artificial Orthopedic Implants," Nanomedicine, 2(6):861-874 (2007).
Kuchibhatla, et al, "One Dimensional Nanstructured Materials," Progress in Materials Science, 52:699-913 (2007).
Jones, Jr, "New Trends in Bioactive Scaffolds: The Importance of Nanostructure," Journal of the European Ceramic Society, 29:1275-1281 (2009).

* cited by examiner

*Primary Examiner* — Karen Cochrane Carlson
*Assistant Examiner* — Natalie Moss
(74) *Attorney, Agent, or Firm* — Howard Eisenberg, Esq

(57) ABSTRACT

Nanostructures such as nanowires, nanosprings, nanorods, and nanoparticles, when maintained in contact with a source of bone cells, enhance the proliferation of the bone cells and integration bone into the nanostructures. The nanostructures may or may not be coated with a metal or metal oxide coating and preferably are textured. Such coated or non-coated nanostructures may be utilized on the surface of bone implants to enhance osseointegration of the implants.

13 Claims, 2 Drawing Sheets

METHOD FOR STIMULATING OSTEOGENESIS

This application claims priority from U.S. Provisional Patent Application No. 61/419,152, filed on Dec. 2, 2010.

FIELD OF THE INVENTION

The present invention pertains to the field of nanostructures, such as nanotubes, nanosprings, nanorods, and nanoparticles, and to the field of mats comprising such nanostructures, and to methods of use of such nanostructures to stimulate osteogenesis.

BACKGROUND OF THE INVENTION

Treatment of disorders of the musculoskeletal system, such as skeletal deformities and traumatic injuries that result in fractures, frequently involve the use of orthopedic implants. Of key importance in this field is the assurance that orthopedic implants are permanently and securely set in place. Implant failure can result in additional surgical procedures, severe discomfort to the patient and delay of rehabilitation. Moreover, the overall cost of revision surgery frequently exceeds the cost of primary intervention and poses an additional risk to the patient.

The most common cause of orthopedic implant failure is a suboptimal bone-implant interface, caused by the lack of integration of the implant into the bone structure (osseointegration), frequently leading to aseptic loosening. The process of osseointegration involves the bone healing around and incorporating into the surface of the orthopedic device. Healing occurs as specialized cells, osteoblasts, secrete both the organic and inorganic components of the bone matrix, which is a gel-like substance that becomes mineralized during the healing process. It is this mineralization that sets the implant in place and provides integration of the material of the implant into the bone. Thus, the design of implants materials and coatings that promote mineralization and osseointegration is a high priority in the orthopedics field.

The main osseointegration coatings that are in clinical use today are metal oxide micron beads, hydroxyapatite crystal coatings, calcium phosphate composites (Ca—P), bioactive glass, and titanium (Ti) and titanium alloy films. Both the titanium alloy films and micron beads have been shown to adhere effectively to the bone and expedite osseointegration. Titanium alloy and hydroxyapatite crystal coatings have been shown to increase healing time significantly and are currently in use for dental implants, pins, screws, and femoral stems in hip replacements. Similarly, Ca—P has been used to coat titanium devices and is known to stimulate bone formation and to intensify bonding strength. Bioactive glasses composed of different proportions of $SiO_2$, $Na_2O$, $CaO$, and $P_2O_4$ are osteogenic and allow osteoblasts to migrate through the material.

Although all of these coatings may successfully be used clinically, they have inherent limitations including low volumetric porosity, high modulus of elasticity, low frictional characteristics compared to natural bone, and reduced longevity. For instance, the high temperature process needed to deposit titanium nitride on the surface of an implant can amplify cracks and increase the fatigue rate of the implant. Furthermore, the titanium nitride coatings have been shown to release metal ions over time and show wear defects after maintaining loads for a year. Both the bioactive hydroxyapatite crystals and Ca—P coatings tend to fail due to interfacial fracture or delamination between the implant and bone. Similarly, while silicate-based glasses can be used to coat titanium implants, apatite, a mineral component of bone, does not form well on such surfaces and the mechanical properties of glass do not allow the high loads frequently encountered by orthopedic implants. Consequently, the shortcomings of the current coatings underlie the need for new materials that can increase osseointegration of implants.

The method of production of nanostructures, especially silicon dioxide nanostructures, the binding of nanostructures onto a surface of a substrate material, the optional coating of nanostructures, and several uses of coated and uncoated nanostructures are disclosed in International Applications PCT/US2006/024435 and PCT/US2010/053880, U.S. Pat. No. 7,771,512, and U.S. Patent Application No. 2010/0215915, the disclosures of which are incorporated herein in their entirety. These patent documents disclose how the nanostructures are made and their use in fields such as for gas sensors, optical sensors, molecular sensors, hydrogen storage devices, catalytic converters, and for photocatalytic conversion of carbon dioxide.

Recently, several authors have disclosed the use of nanomaterials to increase bone cell proliferation and osteogenesis. Oh et al, Journal of Biomedical Materials Research Part A, DOI:10.1002/jbm.a (2006), discloses an increase in osteogenesis obtained with vertically aligned titanium dioxide nanotubes. Ruckh et al, Nanotechnology, 20 (2009) 045102 (7 pp), similarly discloses that an increase in osteogenesis is obtained with vertically aligned tantalum oxide nanotubes. None of these materials has been approved for use in veterinary or human medicine and problems persist with these nanostructural implants.

The prior art dealing with nanostructures and osseointegration concerns vertically aligned nanostructures, specifically nanotubes. Such structures provide a less than ideal substrate for osteogenesis because the aligned nanostructures do not form a nanostructure mat in which the nanomaterials are disordered and inter-related in a morphology similar to that which is formed by connective collagen networks found in healing bone. Thus, a need exists for a nanostructure that more closely mimics the structure of such collagen and that will be more suitable for the stimulation of osseointegration.

DETAILED DESCRIPTION OF THE INVENTION

Figure 1:
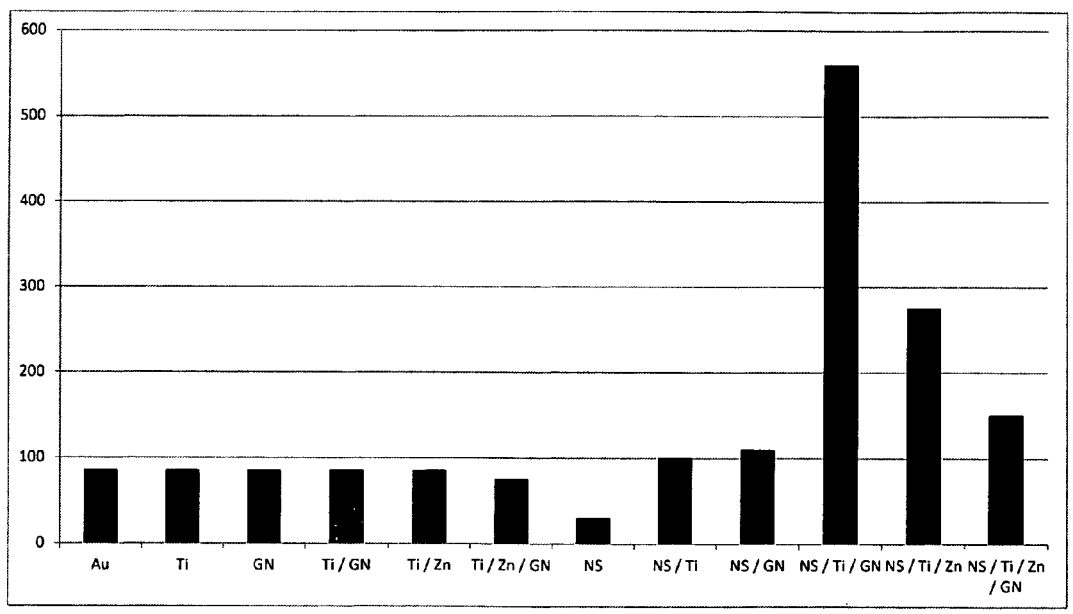
FIG. 1 is a bar graph showing proliferation of normal human osteoblasts on day on various glass discs with gold coating (Au), titanium coating (Ti), gold nanoparticles (GN), titanium coating and gold nanoparticles (Ti/GN), titanium coating and zinc oxide coating (Ti/Zn), titanium coating, zinc oxide coating, and gold nanoparticles (Ti/Zn/GN), bare silicon dioxide nanosprings (NS), silicon dioxide nanosprings with titanium coating (NS/Ti), silicon dioxide nanosprings with gold nanoparticles (NS/GN), silicon dioxide nanosprings with titanium coating and gold nanoparticles (NS/Ti/GN), silicon dioxide nanosprings with titanium coating and zinc oxide coating (NS/Ti/Zn), and silicon dioxide nanosprings with titanium coating, zinc oxide coating, and gold nanoparticles (NS/Ti/Zn/GN). The Y axis is cell count.

It has been discovered that proliferation of bone cells and/or deposition of bone matrix, two components of osteogenesis, are enhanced by allowing bone cells to grow in association with a multiplicity of nanostructures that are in the form of a nanostructure mat. It has further been discovered that a nanostructure mat comprising nanostructures that are textured with nanoparticles provides additional enhancement of bone cell proliferation and/or deposition of bone matrix.

As used herein, the term "nanostructures" means an object of intermediate size between molecular and microscopic (micrometer-sized) structures. Included within the term "nanostructures" are two-dimensional nanostructures such as nanowires, nanorods, nanotubes, and nanosprings, and three-dimensional structures such as nanoparticles.

As used herein, the term "nanowire" means a wire that has a diameter of 100 nm or less and that has a length that is at least 5 times greater than its diameter.

As used herein, the term "nanorod" means a nanostructure that is similar to a nanowire but has a length that is between 3 and 5 times greater than its diameter.

As used herein, the term "nanotube" means a tubular structure that has a diameter of 100 nm or less and that has a length that is at least 3 times greater than its diameter. A nanotube may be considered to be a nanowire, nanospring, or a nanorod with a tubular structure.

As used herein, the term "nanospring" means a nanowire or nanotube that is in the form of a coil, such as a helix. The term "nanospring" includes nanosprings that consist of a single nanowire and nanosprings that contain multiple nanowires that are intertwined to form a coil.

As used herein, the term "nanoparticle" means an object that has a length that is between 1 and 3 times that of its width and in which the length is 100 nm or less.

As used herein, the term "nanostructure mat" or "mat of nanostructures" means a structure made up of non-unidirectional tangled, adhering, or intertwined filaments or strands of nanostructures such as nanosprings, nanotubes, nanowires, or nanorods. A nanostructure mat provides a porous network upon which cells, such as bone cells, may proliferate. The nanostructure mat may be bound to a solid substrate or may be independent of a solid substrate.

As used herein, the term "textured" when referring to a nanostructure means a nanostructure having geometrical irregularity on its exposed surface, such as by the presence of nanoparticles on the surface of nanowires, nanosprings, or nanorods, or on the outer surface of nanotubes.

Thus, in one embodiment, the present application provides a method for enhancing the proliferation of bone cells and/or the deposition of bone matrix. According to this embodiment, a multiplicity of bone cells are situated in association with a multiplicity of nanostructures in the form of a nanostructure mat and the bone cells and the nanostructures are permitted to remain in association for a time sufficient for the bone cells to proliferate and/or for new bone matrix to be deposited. Preferably, the nanostructures are textured. It has been determined that, in addition to the proliferation of the bone cells, new bone matrix is formed and calcium is deposited within the matrix, which indicates that new bone is formed on the surface of the nanostructures.

In a preferred embodiment, the nanostructures are composed of silicon dioxide, which is preferred because it is biocompatible and is resistant to damage by sterilization methods. Nanomaterials other than silicon dioxide, such as ceramic or metal-based nanostructures may be utilized. When utilizing nanostructures made of silicon dioxide, it is preferred to coat the nanostructures with a metal or metal-based coating, such as an oxide, for example of titanium, zinc, or an alloy or an oxide of these materials. The coating may be between the nanostructures and texture-providing nanoparticles if present, or may overlay the nanostructures and the nanoparticles. When utilizing nanostructures made of a metal, an alloy, or an oxide of a metal, such as titanium, a coating is not required but may be utilized if desired. For example, titanium nanostructures may be coated with zinc oxide or a metal such as gold.

In one embodiment, the nanostructures that are associated with the bone cells are bonded as a nanostructure mat to a solid substrate. Any solid material that has a melting point higher than the temperature that is utilized to produce and/or bond the nanostructures to it is suitable for the substrate. Examples of suitable solid substrates include glass, metals such as titanium, tantalum, steel, stainless steel, or aluminum, metal oxides such as oxides of titanium or tantalum, and ceramics.

The solid surface may have any shape, as a mat of nanostructures, such as nanosprings, can be made to conform to any geometric shape. Accordingly, the solid surface may be of two dimensions, such as a flat disc, may be a simple geometric solid or hollow shape, such as a sphere, cube, or pyramid, or may have a complex geometric shape.

The nanostructures may be bonded to the solid surface by any method by which nanostructures may be bonded to or formed upon a solid surface. For example, nanostructures, such as silicon nanosprings, may be formed upon a solid surface as described in any of International Applications PCT/US2006/024435 and PCTTUS2010/053880, U.S. Pat. No. 7,771,512, and U.S. Patent Application No. 2010/0215915. For example, nanoparticles may be produced as described in PCT/US2010/053880.

Preferably, the nanomaterials are textured with the presence of nanoparticles, which are preferably metal nanoparticles, situated on the surface of the nanostructures. It has been determined that the presence of nanoparticles on the nanostructures enhances osteogenesis beyond that which is obtained with smooth nanomaterials. Virtually any metal with ligands that has a vapor pressure can be used for the metallization process. Examples of suitable metals include gold, silver, copper, nickel, and platinum. In addition to enhancing osteogenesis and osseointegration, the nanoparticles on the surface of the nanostructures forming the mat may decrease the risk of osteomyelitis or other infection when utilized in the body.

The solid surface to which the nanostructure mat is attached is contacted with a source of bone cells, such as osteoblasts, and the nanostructures and the bone cells are permitted to interact for a time sufficient to permit the generation of new bone cells and/or the production of bone matrix. Generally, the nanostructures and the bone cells remain in association for a period of at least two days.

In one preferred embodiment, nanostructures, such as nanosprings, that are attached to a solid surface such as a glass slide are provided and osteoblasts are added to the glass slides. In another preferred embodiment, an irregular solid surface, such as a titanium alloy bone implant having a surface that is bonded to a mat of nanostructures such as nanosprings, is exposed to a source of osteoblasts. Such exposure may be in vitro or may be in vivo, such as by inserting the implant into the body of an animal, such as on a bone. Bone cells are shown to proliferate on the solid surfaces bonded to the mat of nanostructures at a faster rate than occurs when such solid surfaces lacking the mat of nanostructures are exposed to osteoblasts in an identical manner.

For example, a nanostructure mat as described herein may be provided on the surface of a bone implant device, such as a plate, pin, or screw, and the implant may be placed in association with a source of osteoblasts by placement and fixation onto or into a bone in the body of a human or veterinary patient.

In another embodiment, the nanostructures are free, that is they are not bonded to a solid surface, at the time that the nanostructures are exposed to bone cells. According to this embodiment, nanostructures such as nanosprings are made, such as by the method described above and the nanostructures are then harvested off of the substrate on which they are bound to yield free nanostructures. The free nanostructures can be used in the form of a free nanostructure mat as a matrix that may further include proteins or other materials such as poly-methyl-methacrylate or bone morphogenic protein-2. The matrix, with or without the presence of bone cells, may be applied to a source of osteoblasts, such as a bone defect, to stimulate the production of new bone cells and/or increase bone matrix deposition. In this way, the nanostructure matrix may be used to repair damaged bone or as a bone packing material.

The nanomaterials described herein, thus are useful in the field of bone and cartilage regeneration. They provide structural and morphologic support for bone growth and have the capability to promote proliferation, differentiation, and deposition of calcium. Moreover, because the nanomaterials can be grown on random shapes and sizes of substrates, new bone can be custom made for individual patients.

The nanomaterials described herein may be used to promote the growth of bone cells of any animal in which bone cells are present. Thus, the method described herein is useful in any vertebrate animal, including amphibians, reptiles, birds, and mammals. With regards to mammals, the method may be used with humans and with veterinary animals, such as farm animals such as horses, cows, goats, sheep, llamas, and swine, domesticated animals such as dogs and cats, and laboratory animals such as monkeys, mice, rats, and guinea pigs.

Advantages of the nanostructures described herein include their strong bond to solid structures, lack of laminate separation from the solid structures, and biocompatibility. Additionally, because the nanostructures are not damaged by exposure to temperatures and chemicals used in sterilization, the nanostructures, either free or attached to a solid substrate, are easily sterilized for use in medical applications.

Other advantages of the nanostructures described herein include their ability to increase the production and differentiation of osteoblasts, their ability to increase bone matrix deposition from osteoblasts, their ability to integrate bone matrix into the scaffolding of the nanomaterial structure, their applicability to any shape or size of device, and their resistance to harm due to sterilization methods.

The invention is further illustrated in the following non-limiting examples.

EXAMPLE 1

Production of Nanostructure Mats

Nanospring mats were grown on 12 mm diameter microscope cover glass discs (Fisher Scientific Co., Pittsburgh, Pa.) by a vapor-liquid-solid (VLS) mechanism utilizing in an atmospheric furnace at a constant O2 flow rate using a gold layer as a catalyst and a silicon precursor, as disclosed in U.S. Patent Application No. 2010/0215915, paragraph 0041. The growth time to produce an 80 µm thick nanospring mat was approximately 15 minutes.

EXAMPLE 2

Coating of Nanostructure Mats

The nanosprings of Example 1 were coated with zinc oxide (ZnO) and/or titania ($TiO_2$) as described in George et al, Surface Chemistry for Atomic Layer Growth, Journal of Physical Chemistry [Internet] 100(31):13121-13131 (1996) and Elam et al, Rev. Sci. Instrum. [Internet] 73(8):2981 (2002). The nanosprings were coated by atomic layer deposition (ALD) in a tube furnace maintained at 170° C. for diethyl zinc and 300° C. for titanium tetrachloride ($TiCl_4$). Between each pulse of precursor, or water, which is used as a reactant, the system was purged with $N_2$ to ensure that the precursors reacted only at the surface of the growing film.

EXAMPLE 3

Nanoparticle Texturing of Nanostructure Mats

The coated or uncoated nanosprings of Examples 1 and 2 were coated with gold nanoparticles to provide a textured surface. The nanosprings were immersed in a gold tetrachloride ($AuCl_4$) solution in reagent grade alcohol. After air-drying at room temperature, the samples were reduced in an atmosphere of $H_2$ and Ar for 15 minutes at 300° C. The samples were then cooled to room temperature in an Ar atmosphere to avoid oxidation.

EXAMPLE 4

Sterilization of Nanostructure Mats

The nanostructures were examined visually using field emission scanning electron microscopy prior to sterilization. It was determined that the silica nanosprings formed helical structures characteristic of this nanomaterial and that the nanospring density on the glass discs ranged from 0.71 to 1.01 $mg/cm^2$. The glass slides covered with bare or coated silica nanosprings were subjected to typical sterilization techniques to verify that the nanostructure mats could resist heat sterilization. The glass discs with nanostructure mats of Examples 1 to 3, were rinsed with deionized water and then washed for 10 minutes in 70% ethanol. The samples were air dried and placed in autoclave sleeves and then conventionally autoclaved for 20 minutes.

It was determined that the nanostructures could withstand sterilization temperatures (134° C.) and pressures (4 PSI or 207 torr) for 35 minutes in an autoclave. Attachment of the nanostructures to the glass discs was maintained throughout the autoclaving procedure and FESEM analysis showed no effect on the integrity or the structure of the nanostructures.

EXAMPLE 5

Growth of Osteoblasts

Sterilized discs containing nanostructure mats were placed in wells of tissue culture 24 well plate and were rinsed with osteoblast growth medium (OGM) (Lonza, Inc., Williamsport, Pa.). Fresh OGM was then added and the plates were incubated at 5% $CO_2$ at a temperature of 37° C. for 30 minutes before adding osteoblasts.

10,000 osteoblast cells were added to each well containing glass cover slips. The plates were incubated at 37° C., 5% $CO_2$ for 5 days. At days 1 and 3, culture media was replaced with 0.2% calcein blue (Molecular Probes/Invitrogen, Carlsbad, Calif.) in OGM and the plates were incubated for 15 minutes at 37° C. with 5% $CO_2$. Calcein blue stain was then rinsed twice with N'-2-hydroxyethylpiperazine-N'-Ethane-sulfonic Acid (HEPES, pH 7.37, Lonza Inc.) and stained cells, which represent live cells, were counted in 5 views at 200× using a Zeiss Axiovert 40 CFL microscope. After counting, cells were washed 3 times with warm OGM and returned to tissue culture incubator to continue growth. At day 5 of the experiment cells were terminally stained with Vybrant® Green (Invitrogen) to detect all cells and propidium iodide (PI) (Invitrogen) to detect dead cells. Wells were rinsed twice with HEPES followed by addition of 0.06% PI, 0.16% Vybrant® Green in PBS. After 20 min incubation at 37° C., the wells were washed with PBS two times. Cells were visualized at 200× with Zeiss Axiovert 40 CFL microscope, and the number of Vybrant® Green positive and PI positive cells on 5 fields of view was counted. Images of characteristic fields of view were captured using a Canon Powershot G6 camera.

To determine the ability of normal human osteoblasts to grow on the nanostructures, the same number of cells was added to wells in tissue culture plates that contained either bare glass discs (hereafter referred to as normal growth condition) or uncoated silicon dioxide nanospring-covered glass discs. Cell growth was monitored by microscopy 4 days after the start of the experiment and it was noted that, while cells proliferated under normal growth conditions, very few cell could be detected on the nanospring covered glass slip.

Growth of osteoblasts was then evaluated with silicon dioxide nanosprings that had been coated with $TiO_2$ and with gold nanoparticles or with ZnO coating. Results are shown in FIG. 1. Cells proliferated well, as determined by microscopy, on the coated $SiO_2$ nanosprings.

In order to establish that the cells that were grown on the nanosprings were alive and that neither the nanosprings nor the coatings were lethal to the osteoblasts, the cells were grown for 5 days on either normal conditions or on Au/TiO2 coated nanosprings with Vybrant® Green, a dye that stains the nucleus of cells and with propidium iodide, which preferentially stains dead cells. In addition, cells grown on normal growth conditions were treated with ethanol, which induces death, to serve as a positive control for the presence of dead cells. Quantification of the staining experiment showed similar levels of cell death in both normal growth and TiO2/Au coated nanosprings (19±9% and 10±2% respectively), whereas ethanol killed most (96±4%) of the osteoblasts. This test established that the nanosprings coated with titanium and gold particles support osteoblast growth and do not affect cell viability.

A higher number of cells were noted consistently on coated nanospring compared to the normal growth conditions. Even though both samples always started with the same number of osteoblasts, as early as 24 hours a significant difference in cell numbers was detected between the controls and the coated nanosprings samples. To quantify this observation, the same number of cells were seeded on plain coverslips or on coverslips covered with nanosprings and the numbers of live cells after 5 days of growth were counted.

In addition, to compare different nanospring coatings, nanosprings coated with gold nanoparticles (Au) or titania ($TiO_2$) or with a combination of gold nanoparticles and titania, with or without zinc oxide coating (ZnO) (i.e. $TiO_2$/Au, $TiO_2$/ZnO and $TiO_2$/Au/ZnO) were made. All of these nanospring samples were manufactured at the same time to ensure uniform properties of nanospring mats and equal coating amounts. Coating densities were calculated to be 0.5±0.05 mg/cm$^2$ for titania, 3.0±0.05 mg/cm$^2$ for zinc oxide, and 0.015±0.003 mg/cm$^2$ for gold nanoparticles.

At the end of the 5-day incubation of normal human osteoblasts on the different discs, the number of cells was determined to be significantly greater on the glass coverslips containing nanosprings coated with either $TiO_2$/Au, and $TiO_2$/Au/ZnO, when compared to either plain coverslips, coverslips with nanosprings alone or nanosprings with either $TiO_2$ or Au.

Consistent with our initial observation, silicon dioxide nanosprings without a coating decreased the proliferation of osteoblasts. The nanosprings coated with $TiO_2$ and ZnO also showed an increase in the number of cells as compared to normal growth conditions albeit not as great as what was observed with coating combinations that contain Au nanoparticles (i.e. $TiO_2$/Au and $TiO_2$/Au/ZnO). Thus, coated silicon dioxide nanosprings significantly enhance the growth of human osteoblasts and could potentially serve as a scaffold for bone regeneration.

These proliferation studies establish that osteoblasts divide at a faster rate when grown on silicon dioxide nanosprings containing a coating and nanoparticles. To further exemplify this finding, the same numbers of cells were added to plain coverslips and coverslips containing silicon dioxide nanosprings with those two different coatings and the numbers of live cells were counted after 24, 72 and 120 hours. While the doubling rate between 24 and 120 hours for cells grown on plain glass was every 22.2 hours, cells grown on silicon dioxide nanosprings with $TiO_2$/Au and with $TiO_2$/Au/ZnO double their numbers every 8.2 and 14.4 hours respectively, during the same time period. Thus silicon dioxide nanosprings coated with titania and gold nanoparticles accelerate the division of osteoblasts by almost three times of what is observed under normal growth conditions.

It is conceivable that osteoblasts, when grown on silicon dioxide nanosprings, could be transformed to faster dividing cells, due to either mutations or differentiation into a different type of cell. Therefore, in order to determine whether the fast proliferative phenotype of osteoblasts grown on the nanosprings constitutes a permanent change in the cells, the proliferation rate of cells previously grown on the nanosprings was tested. For this purpose, cells grown for 4 days on either normal cell culture conditions, $TiO_2$/Au coated nanosprings, or $TiO_2$/Au/ZnO coated nanosprings were harvested and the same number of cells was added to plain cover slips to monitor their growth. It was found that, regardless of how the cells were grown previous to the test, the same number of cells 4 days later was observed. This finding establishes that the high proliferation rate of the cells grown on nanosprings is a reversible trait and that the nanosprings do not permanently transform the cells.

EXAMPLE 6

Alkaline Phosphatase Measurements

Osteoblasts differentiate into cells that produce bone matrix, collagen, and many other osteogenic factors for osseointegration, which process involves the differential expression of certain proteins. One of these proteins, alkaline phosphatase, can be used as a biomarker to determine whether and to what level, osteoblasts have differentiated into matured bone forming cells. Therefore, the levels of alkaline phosphatase activity of cells grown for 36 days on either normal conditions or on nanosprings coated with the various materials used in the proliferation studies was determined.

Control glass discs and the respective nanostructure containing discs were placed in 24-well plates and a total of 10,000 osteoblasts were added to each of the wells. Cultures were then incubated at 37° C., 5% $CO_2$ in OGM for 36 days. To maintain the pH and nutrient levels, media was changed every 4 days during this incubation period. At the end of the 36 days incubation, discs were carefully removed from the wells and placed into empty wells and then washed with PBS two times before adding TRITON® X-100 (Dow Chemical Co., Midland, Mich.) at 1% (500 μl/well) to lyse cells. The plates were incubated for 2 hours at 37° C., 5% $CO_2$ and then lysates were transferred into microcentrifuge tubes and three rounds of freeze/thaw cycles were done at −80° C. QuantiChrom™ Alkaline Phosphatase Assay (BioAssay Systems, Hayward, Calif.) was used to test alkaline phosphatase levels according to manufacturer's instructions. As part of this process an EL 808 ultra microplate reader (Biotek Instruments Inc., Winooski, Vt.) spectrometer was used to read emission at 450 nm. The readout of alkaline phosphatase activity was normalized by determining total protein level for each sample. Protein levels were determined using the BCA protein assay (Thermo Fisher Scientific, Inc., Rockford, Ill.) according to manufacturer's instructions.

Figure 2:
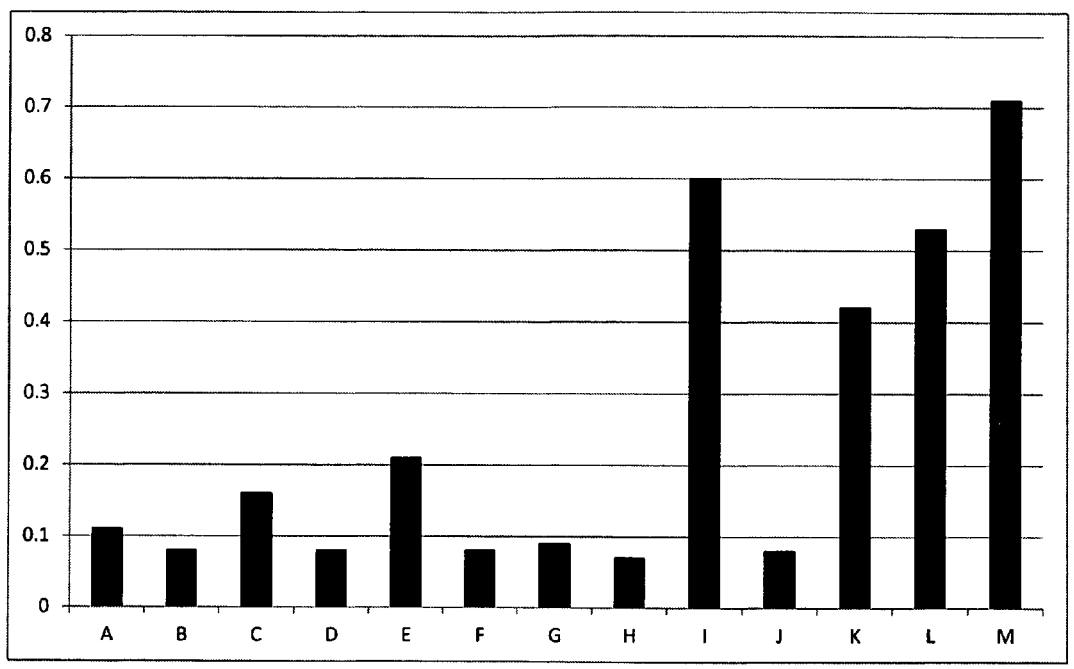
FIG. 2 is a bar graph showing alkaline phosphatase levels of osteoblasts on various glass discs with (A) no coating or nanostructures, (B) gold sputtered droplets, (C) gold nanoparticles, (D) titanium oxide coating, (E) titanium oxide coating and gold nanoparticles, (F) titanium oxide and zinc oxide coatings, (G) titanium oxide and zinc oxide coatings, and gold nanoparticles, (H) uncoated silicon dioxide nanosprings, (I) silicon dioxide nanosprings with titanium dioxide coating, (J) silicon dioxide nanosprings with gold nanoparticles, (K) silicon dioxide nanosprings with titanium coating and gold nanoparticles, (L) silicon dioxide nanosprings with titanium and zinc oxide coatings, and (M) silicon dioxide nanosprings with titanium and zinc oxide coatings and gold nanoparticles.

Results are shown in FIG. 2. While cells grown on plain nanosprings and Au particle silicon dioxide nanosprings showed similar levels of alkaline phosphatase as those grown on normal conditions, osteoblast grown on the $TiO_2$, $TiO_2$/Au, $TiO_2$/ZnO and $TiO_2$/Au/ZnO coated silicon dioxide nanosprings exhibited significantly more alkaline phosphatase activity (4.70, 3.27, 4.16, and 5.57 times more, respectively) than control cells. Thus, coated silicon dioxide nanosprings not only enhance the rate at which osteoblast divide, but also increase the ability of osteoblasts to develop into mature forms of this type of cells.

EXAMPLE 7

Calcium Deposition Studies

Calcium salt deposition by bone cells is one of the key cellular events needed for effective osseointegration because it leads to mineralization of the bone matrix. Accordingly, the ability of coated silicon dioxide nanosprings to promote calcium deposition was determined.

Osteoblast growth media (OGM) was supplemented with hydrocortisone (200 nM) and β-glycerophosphate (2.0 mM). 10,000 cells per sample were added to the OGM and the cultures were incubated at 37° C., 5% $CO_2$ for 36 days while changing media every 3-4 days. Mineral staining was done with Von Kossa stain system (American MasterTech Scientific, Lodi, Calif.). In brief, media was removed and 2 ml of formaldehyde with phosphate buffered saline (PBS) (1:9) was added to each well and incubated for 20 minutes. All samples underwent a serial alcohol dehydration process (70% ethanol for 10 minutes, 80% for 10 minutes, 90% for 20 minutes, and rinse with absolute alcohol). Each sample was then rinsed three times with deionized water. Staining was performed according to the manufacturer's directions. The disks were viewed under light microscopy. Dark brown or black metallic silver stain positively identifies phosphate anions of the calcium salt deposition whereas the cells stained red. Imaging was done using a Leica MZ16F fluorescent stereoscope, a Leica DFC420 color digital camera and Leica Application Suite software (Leica Microsystems, Inc., Buffalo Grove, Ill.).

Using this approach, a significant number of dark spots were detected as well as a uniform dark brown staining with cells grown for 36 days on the TiO2/ZnO/Au coated nanosprings. The coated nanosprings without cells reacted with the stain to produce a light purple background staining. However, comparing the various nanospring samples with and without cells showed clear differences in the color and darkness, indicating that calcium salt were deposited in the samples containing cells. In contrast, there was minimal deposition of calcium salt nodules with the cells grown under normal conditions as indicated by the lack of detectable brown or black spots, although many cells (red staining) were present. Thus, consistent with the fact that cells grown on coated silicon nanosprings differentiate into bone forming cells, these cells exhibit the ability to deposit calcium salts, an indicator of calcium deposition.

In order to establish the presence of bone matrix in the samples, the samples were directly visualized using FESEM at a magnification of 10.00 KX. While normal growth cultures showed some clusters of hydroxyapatite crystals, they contained dramatically less crystal formations than the cultures grown on coated nanosprings, which were almost completely covered uniformly in crystals.

To confirm and quantify the mineralization of cultures grown on coated nanosprings, energy dispersion spectroscopy (EDS) on the Van Kossa stained samples was performed in order to measure the amounts of various elements. Cells grown on the coated silicon dioxide nanosprings showed the highest amounts of calcium and phosphorus deposition.

Various modifications of the above described invention will be evident to those skilled in the art. It is intended that such modifications are included within the scope of the following claims.

The invention claimed is:

1. A method for osteogenesis comprising contacting bone cells to silicon dioxide nanosprings in the form of a nanostructure mat, which nanosprings are coated with a film of a first metal or metal-based coating and a film of a second metal or metal-based coating overlying the first coating, wherein the first coating is zinc or zinc-based and the second coating is titanium or titanium-based or the first coating is titanium or titanium-based and the second coating is zinc or zinc-based, and maintaining the contact of the nanosprings and the bone cells for a time sufficient for bone cells to proliferate and/or for the bone cells to deposit bone matrix on the nanosprings.

2. The method of claim 1 wherein the nanosprings of the nanostructure mat are bound to a solid surface.

3. The method of claim 1 wherein the nanosprings are not bound to a solid surface.

4. The method of claim 2 wherein the solid surface is metallic.

5. The method of claim 4 wherein the metallic solid surface is titanium or titanium oxide.

6. The method of claim 2 wherein the solid surface is glass.

7. The method of claim 1 wherein the coatings are titanium or titanium oxide and zinc or zinc oxide.

8. The method of claim 1 wherein the nanosprings are textured.

9. The method of claim 8 wherein the nanosprings are textured by the presence of nanoparticles on the nanosprings.

10. The method of claim 9 wherein the first coating is between the nanosprings and the nanoparticles.

11. The method of claim 9 wherein the first coating overlays the nanosprings and the nanoparticles.

12. The method of claim 1 wherein the nanosprings are textured with metal nanoparticles and coated with the first metal or metal-based coating and the second metal or metal-based coating overlying the first coating.

13. The method of claim 10 wherein the first and second coatings are between the nanosprings and the nanoparticles.

* * * * *

UNITED STATES PATENT AND TRADEMARK OFFICE
CERTIFICATE OF CORRECTION

| | | |
|---|---|---|
| PATENT NO. | : 8,728,464 B2 | Page 1 of 1 |
| APPLICATION NO. | : 13/135933 | |
| DATED | : May 20, 2014 | |
| INVENTOR(S) | : Jamie Hass | |

It is certified that error appears in the above-identified patent and that said Letters Patent is hereby corrected as shown below:

Title Page should read as follows:

(12) United States Patent
    Hass

(75) Inventor: Jamie Hass, Pinehurst ID (US)

Signed and Sealed this
Twelfth Day of August, 2014

Michelle K. Lee
*Deputy Director of the United States Patent and Trademark Office*